United States Patent [19]

Grögler et al.

[11] Patent Number: 5,159,046
[45] Date of Patent: Oct. 27, 1992

[54] PROCESS FOR THE PREPARATION OF HIGHLY ELASTIC PLASTICS

[75] Inventors: Gerhard Grögler; Andreas Ruckes, both of Leverkusen; Richard Kopp, Cologne; Heinrich Hess, Cologne; Robert Eiben, Cologne; James M. Barnes, Wermelskirchen, all of Fed. Rep. of Germany

[73] Assignee: Bayer Aktiengesellschaft, Leverkusen, Fed. Rep. of Germany

[21] Appl. No.: 543,649

[22] Filed: Jun. 26, 1990

[30] Foreign Application Priority Data

Jul. 4, 1989 [DE] Fed. Rep. of Germany ....... 3921861

[51] Int. Cl.⁵ .............................................. C08G 18/00
[52] U.S. Cl. .......................... 528/44; 528/60; 528/68; 521/65; 521/68
[58] Field of Search .......... 521/51, 159, 65, 68; 528/68, 44, 60; 265/75 NT, ; 264/267

[56] References Cited

U.S. PATENT DOCUMENTS

| | | | |
|---|---|---|---|
| 3,124,605 | 3/1964 | Wagner | 525/472 |
| 3,769,265 | 10/1978 | Grogler | 265/75 NT |
| 4,028,392 | 6/1977 | Ogawa et al. | 528/59 |
| 4,228,249 | 10/1980 | Blahak et al. | 521/159 |
| 4,416,844 | 11/1983 | Wyman | 264/267 |
| 4,483,974 | 11/1984 | Grogler et al. | 528/68 |
| 4,576,970 | 3/1986 | Ganster et al. | 521/51 |
| 4,851,567 | 7/1989 | Ruckes et al. | 560/330 |

FOREIGN PATENT DOCUMENTS 3725198 2/1989 Fed. Rep. of Germany .
58-098327 6/1983 Japan .

OTHER PUBLICATIONS

Polyurethane Handbook, Edited by G. Oertel, Macmillan Publishing Co., Inc., New York (1985) pp. 8-9.

Primary Examiner—Morton Foelak
Assistant Examiner—Duc Truong
Attorney, Agent, or Firm—Joseph C. Gil; Richard E. L. Henderson

[57] ABSTRACT

The present invention relates to a process for the preparation of a modified 1,5-naphthylene diisocyanate containing urea and biuret groups comprising reacting
(a) 1,5-naphthylene diisocyanate in molten form with
(b) a mixture comprising about 0.02 to about 0.5 mole of water per mole of 1,5-naphthylene diisocyanate and about 1 to about 10 parts for each part of water of an organic solvent.

The present invention further relates to a process for the preparation of elastomeric moldings comprising reacting by the one-shot or prepolymer process at an isocyanate index of 70 to 130 a modified 1,5-naphthylene diisocyanate containing urea and biuret groups with compounds containing at least two isocyanate-reactive groups and having a molecular weight in the range from about 500 to about 10,000 and, optionally, organic compounds containing isocyanate-reactive groups and having a molecular weight in the range from 60 to 499.

13 Claims, No Drawings

PROCESS FOR THE PREPARATION OF HIGHLY ELASTIC PLASTICS

BACKGROUND OF THE INVENTION

This invention relates to a process for the preparation of a modified 1,5-naphthylene diisocyanate ("NDI") containing urea and biuret groups.

The production of crosslinked plastics from linear polyesters or polyethers containing hydroxyl groups using organic diisocyanates in a quantity in excess of that required for reaction with the hydroxyl groups has long been known. In this reaction, the polyester or polyether chains are crosslinked by urethane groups and linear structures having free isocyanate groups at the chain ends are formed. The molecular weight of these so-called linear isocyanate polyesters or polyethers is greater when using a smaller excess of diisocyanate over the quantity required for reaction with the hydroxyl groups and vice versa. The isocyanate polyesters or polyethers thus obtained may be converted into high-quality crosslinked plastics by essentially three processes.

The first process (German Patentschrift 831,772) involves reacting the polyesters or polyethers containing isocyanate groups with glycols. In this reaction, the isocyanate polyesters or polyethers are first extended via urethane groups and in a second step additional isocyanate groups react with the urethane NH groups to crosslink the molecule via allophanate bonds. This process allows processing in the liquid phase and enables various moldings to be produced by casting without the use of solvents.

The second process uses diamines instead of glycols. The isocyanate polyester or polyether are extended via two adjacent urea groups in which the NH groups react with remaining isocyanate groups to form biuret bonds, the reaction being accompanied by crosslinking.

The third process involves reacting the polyesters or polyethers containing isocyanate groups with water so that an additional two isocyanate groups are attached by urea linkages. A high-molecular weight product is obtained in this way. Here, too, the hydrogen atoms of the ureas react with excess isocyanate groups to form crosslinking biurets. Because such biuret groups are thermally more stable than the allophanate groups described in the first process, the elastomers produced by the second or third process show better mechanical properties, as reflected in particular by their structure, elasticity, compression set, and abrasion. However, the third process has the disadvantage that carbon dioxide is given off during the reaction of the isocyanate groups with water. Consequently, the material cannot be processed in the liquid phase because of the bubbles evolved. Accordingly, processing must be carried out by a complicated method in which the foam-like polyurethane material is compression-molded under high pressure. Compare, for example, Kunststoff-Handbuch, Carl Hanser Verlag, 1966, Vol. VII, pages 270-271. As a result of the numerous individual steps involved, the process can be used only for very demanding applications. Another major disadvantage of the compression-molding step is that it is possible to produce sheeting or moldings of only very simple geometry.

On the other hand, polyisocyanate polyaddition products containing urea groups, particularly polyurethanes containing urea groups, show particularly good mechanical properties. The use of water as chain-extending agent (instead of diamines)-represents a particularly simple and inexpensive method of introducing urea groups. Accordingly, some processes are described in the patent literature in which water is used as chain-extending agent for the reaction of NCO preadducts (two-step process) or of reaction mixtures of polyisocyanates with high molecular weight and/or low molecular weight NCO-reactive compounds (one-step process). These processes are described, for example, in German Offenlegungsschriften 3,407,931 and 3,725,198 and U.S. Pat. No. 4,416,844.

A characteristic feature of this process is that the polyaddition reaction takes place in a closed mold. The carbon dioxide formed during the reaction of the polyisocyanate and water causes a very high pressure increase and, accordingly, remains in the polyaddition product in a partially or even completely dissolved form. After the time required for hardening has elapsed, the moldings may be removed from the mold without undergoing deformation caused by the dissolved $CO_2$. Partly bubble-free solid polyaddition products are obtained, subsequently giving off the dissolved carbon dioxide gradually at room temperature. However, these processes are very complicated.

According to German Offenlegungsschrift 2,107,678, the disadvantages of the processes described above are obviated by introducing the urea groups required for biuret crosslinkage through the actual polyisocyanate, particularly 1,5-diisocyanatonaphthalene. This process is characterized by the use of a modified 1,5-diisocyanatonaphthalene containing from 0.02 to 0.5 mole (preferably from 0.1 to 0.25 mole) of urea and biuret groups per mole of 1,5-diisocyanatonaphthalene. This modified isocyanate is advantageously prepared by heating 1,5-diisocyanatonaphthalene with the corresponding quantity of tertiary alcohols, such as tert-butyl alcohol, for example, to a temperature of 130° C.

Where tert-butyl alcohol is used for the preparation of the modified isocyanate, the tert-butyl urethane of the 1,5-naphthylene diisocyanate initially formed is thermally cleaved with evolution of carbon dioxide and isobutene. Where catalysts, such as hydrohalic acids or salts of nitrogen-containing bases and inorganic or organic acids, are used, the cleavage temperature can be considerably reduced so that a modified 1,5-naphthylene diisocyanate of defined structure is obtained. In the corresponding reaction of this modified 1,5-naphthylene diisocyanate with a linear polyester or polyether, the NCO preadduct containing urea or biuret groups is initially formed and may then be further processed with diols, including low molecular weight or high molecular weight diols. In this phase, the urethane groups as well as the urea groups that are already incorporated may further react with excess isocyanate groups with crosslinking of the molecule. As with crosslinking by glycols or diamines, this reaction is additive. This process is thus a combination of crosslinking by water and glycols or polyols, but with the disadvantages of crosslinking by water being excluded by the urea groups preformed in the polyisocyanate. The advantages of the process over the previously known process are that the crosslinking reaction with diols, particularly with diols of relatively high molecular weight (molecular weight 500 to 6,000), takes place more quickly by virtue of the activating effect of the urea or biuret groups already present in the polyisocyanate and that the end product may therefore be demolded after only a short time. The plastics obtained in this way are rubber-elastic and have good mechanical properties comparable with those of the water-crosslinked polyurethane elastomers (that is, the third process).

A disadvantage of this process, however, is that tertiary alcohols (preferably tert-butyl alcohol) are used as "water donors". The tert-alkyl urethanes initially formed by reaction with the isocyanate are unstable above certain temperatures, particularly in the presence of acidic catalysts, with a gas mixture of carbon dioxide and an unsaturated hydrocarbon being formed. These hydrocarbons are gaseous, flow freely, and have the disadvantage of high inflammability. For ecological reasons, however, these gases can no longer be simply "burned off". Accordingly, the hydrocarbons must be separated or isolated from the gas mixtures with carbon dioxide. This, however, involves a considerable investment in equipment.

German Offenlegungsschrift 2,107,678 discloses that, in addition to hydrogen sulfide and formic acid, water may also be used to modify 1,5-naphthylene diisocyanate. Because of the lack of further concrete disclosures, the following comparative tests were carried out.

The reaction of water and 1,5-naphthylene diisocyanate was first carried out in solvents (for example, ethyl methyl ketone, dioxane or chlorobenzene), the reaction temperatures being increased from 100° to 120°-130° C. In every case, a solid precipitated after only a short time but did not dissolve even after a relatively long reaction time. The resultant solid was the naphthylene diisocyanate urea formed from 2 mole of 1,5-naphthylene diisocyanate and 1 mole of water. Because of its poor solubility, this compound reacts only very sluggishly with the hydroxyl-containing components. After filtration and concentration of the solvent, unchanged NDI is recovered. The NDI thus obtained contains no urea or biuret groups.

Accordingly, another test was carried out without solvent, the reaction of water with NDI (0.1-0.4 mole of water per mole of NDI) being conducted above the melting temperature of NDI (130°-140° C.). A considerable portion of the water was found to condense in the cooling system or on the relatively cold glass walls of the reaction vessel. As a result, this portion of water does not participate in the reaction with NDI. Consequently, the quantity of water cannot be measured exactly. The reaction is further complicated by the increasing deposition of NDI on the relatively cold glass walls caused by the pronounced tendency of NDI to sublime. NDI crusts and NDI-water secondary reaction products, such as NDI polyureas, for example, are immediately formed. This process is also unsuitable for the modification of NDI.

Accordingly, the problem addressed by the present invention is to provide an industrially simple process for the production of modified 1,5-naphthylene diisocyanate containing urea and biuret groups.

It has now surprisingly been found that NDI may readily be modified on an industrial scale if the quantity of water required for the reaction is present in a small quantity of organic solvent. The solvent should preferably have a boiling range of about 80° to about 140° C. and should be miscible with water or should at least form an azeotropic mixture with water in that boiling point range.

SUMMARY OF THE INVENTION

Thus, the present invention relates to a process for the preparation of a modified 1,5-naphthylene diisocyanate containing urea and biuret groups comprising reacting, preferably at a temperature in the range of about 130° to about 160° C., (a) 1,5-naphthylene diisocyanate in molten form with
(b) a mixture comprising about 0.02 to about 0.5 mole (preferably 0.1 to 0.25 mole) of water per mole of 1,5-naphthylene diisocyanate and about 1 to about 10 parts (preferably 2 to 5 parts) for each part of water of an organic solvent.

The present invention also relates to a process for the preparation of elastomeric moldings comprising reacting by the one-shot or prepolymer process at an isocyanate index of 70 to 130 a modified 1,5-naphthylene diisocyanate containing urea and biuret groups prepared according to the above process with (A) compounds containing at least two isocyanate-reactive groups and having a molecular weight in the range from about 500 to about 10,000, and
optionally,
(B) organic compounds containing isocyanate-reactive groups and having a molecular weight in the range from 60 to 499, and
(C) optional auxiliaries and additives.

DETAILED DESCRIPTION OF THE INVENTION

In a preferred process for preparing a modified NDI having urea and/or biuret groups according to the invention, a solvent having a boiling point in the range from about 80° to about 140° C. (preferably in the range from 100° to 120° C.) is used.

In another preferred process for preparing a modified NDI according to the invention, the organic solvent is substantially miscible with water or forms an azeotropic mixture with water in the specified boiling range.

The modified NDI containing urea and biuret groups obtained by the process according to the invention may be advantageously used for the preparation of polyurethane or polyurethane urea elastomers.

In the one-shot process, component (A) and optional components (B) and (C) are combined to form a single "isocyanate-reactive component" which is then reacted in one step with the molten modified NDI containing urea and biuret groups.

In the prepolymer process, the modified NDI polyisocyanate component is allowed to react with at least part of component (A) and, optionally, with part of components (B) and (C) to form a prepolymer containing isocyanate groups. The isocyanate prepolymer is then reacted with a mixture of the remaining quantities of component (A) and optional components (B) and (C).

In a preferred embodiment using the modified NDI containing urea and biuret groups for the preparation of polyurethane or polyurethane urea moldings, the modified NDI according to the invention is, before use, finely ground in suitable mills (particle size 1 to 50 μm and preferably 3 to 20 μm) and the resultant isocyanate powder is used in solid form.

In practice, the solid isocyanate is finely dispersed in the corresponding liquid component (preferably component (A)) by means of a suitable stirrer. Because of the poor solubility of the isocyanate, the finely divided suspension thus obtained remains stable in storage for prolonged periods at temperatures of 10° to 50° C. The solidification process (i.e., polyaddition) then takes place at elevated temperature, a solidification temperature of 100° to 150° C. having proved very favorable.

In a particularly preferred process, the suspension of the solid diisocyanate in the liquid reactive component is mixed with small quantities of an aliphatic diamine, thereby forming a thin polyurea shell on the surface of the isocyanate particles which acts as an anti-diffusion layer. "Deactivated" or "retarded" suspensions formed in this way remain stable in storage at room temperature or even at elevated temperatures of up to 80°-100° C. One-component systems are obtained. Solidification then takes place at any time by heat shock, by which the solid diisocyanate is partly melted and reacts in dissolved form with the NCO-active component. The solidification temperature is in the range from 120° to 150° C. This process is described in U.S. Pat. No. 4,483,974 and European Patent Application EP 103,323.

The preparation of modified NDI containing urea and biuret groups in accordance with the invention, which involves no additional outlay for specialized equipment, is carried out as follows.

A mixture of water and organic solvent is added dropwise with stirring to about 1.0 mole of molten NDI at a temperature of about 130° to about 140° C. The reaction is allowed to continue at a temperature of about 130° to about 160° C. (preferably 130° to 140° C.). The water is used in a quantity of 0.05 to 0.5 mole (preferably in a quantity of 0.1 to 0.25 mole) per mole of NDI. This use of water in admixture with organic solvents is a key feature of the invention. The quantities of solvent used are small compared with the reaction mixture as a whole. If, by contrast, large quantities of solvent are used for dilution, the disadvantages described above arise in the form of the premature precipitation of insoluble oligomeric NDI urea diisocyanates. In addition, the entire solvent must be removed by distillation upon completion of the reaction, involving additional outlay on equipment. In the process according to the invention, therefore, only about 1 to about 10 times (preferably 2 to 5 times) the quantity of solvent, based on 1 part by weight of water, is used.

Suitable solvents have a boiling point in the range from about 80° to about 140° C. (preferably in the range from 80° to 120° C.) and are preferably miscible with water. Examples of such solvents include dioxane, acetonitrile, diethyl carbonate, ethyl methyl ketone, methyl isobutyl ketone, and ethylene glycol dimethyl ether. Less preferably, solvents having only limited miscibility with water may be used but should form an azeotropic water/solvent mixture in the same boiling range. Examples of such solvents include benzene, toluene, xylene, and chlorobenzene.

Carbon dioxide is continuously given off during the addition of the water/solvent mixture to the NDI melt at 130° to 140° C., thereby assuring safe control of the reaction mixture. After the evolution of carbon dioxide has stopped, the solvent and the carbon dioxide still dissolved in the reaction mixture are removed by application of a vacuum. The still liquid reaction product is left to cool and the modified NDI thus formed may be used for the preparation of polyurethanes, either as such or after grinding.

The modified NDI to be used to prepare elastomeric moldings according to the invention is then allowed to react with a compound- containing at least two isocyanate-reactive groups (i.e., component (A)). The isocyanate-reactive compound is preferably a hydroxyl- and /or amino-terminated compound having a molecular weight in the range from about 500 to about 10,000 (preferably in the range from 1,000 to 3,000).

Particularly suitable hydroxyl compounds having at least two hydroxyl groups include known polyesters and polyethers. Suitable polyethers include those obtained by reaction of alkylene oxides, such as ethylene oxide, propylene oxide, epichlorohydrin, or tetrahydrofuran, either alone or initiated with starting compounds. Suitable starting compounds include, for example, water, polyols, or polyamines. Suitable polyols include ethylene glycol, propylene glycol, butanediol, and suitable polyamines include ethylenediamine and hexamethylenediamine. Polyethers of the type suitable for use in accordance with the invention are described, for example, in British Patent 769,091, German Patentschrift 974,371, and U.S. Pat. Nos. 2,948,691 and 2,929,800.

Suitable relatively high molecular weight aminoterminated compounds include polyamino compounds containing aliphatic amino groups such as, for example, those of the type obtained by reductive amination of polyoxyalkylene glycols with ammonia in accordance with Belgian Patent 634,741 and U.S. Pat. No. 3,654,370. Other relatively high molecular weight polyoxyalkylene polyamines may be prepared by methods described in the publication entitled "Jeffamine Polyoxypropylene Amines" (Texaco Chemical Co., 1978), for example, by hydrogenation of cyanoethylated polyoxypropylene glycols (German Offenlegungsschrift 1,193,671), by amination of polypropylene glycol sulfonic acid esters (U.S. Pat. No. 3,236,895), by treatment of a polyoxyalkylene glycol with epichlorohydrin and a primary amine (French Patent 1,466,708), or by reaction of NCO prepolymers with enamines, aldimines, or ketimines containing hydroxyl groups and subsequent hydrolysis in accordance with German Offenlegungsschrift 2,546,536. Other suitable relatively high molecular weight aliphatic diamines and polyamines include polyamines obtainable by alkaline hydrolysis of NCO prepolymers with bases via the carbamate stage in accordance with German Offenlegungsschriften 2,948,419, 3,039,600, and 3,112,118, and European Patent Application EP 61,627, EP 71,132, and EP 71,139.

Suitable polyester starting materials include linear polyesters preferably prepared from substantially saturated aliphatic acid and glycol precursors. Suitable acids include malonic acid, succinic acid, adipic acid, methyl adipic acid, maleic acid, carbonic acid, dihydromuconic acid, thiopropionic acid, diethyl ether dicarboxylic acid, sebacic acid, suberic acid, and higher dicarboxylic acids. Suitable glycols include ethylene glycol, 1,2-propylene glycol, 1,3-propylene glycol, 1,3-butylene glycol, 1,4-butylene glycol, 1,6-hexanediol, methyl hexane-1,6-diol, 1,4-dimethyl-1,3-propylene glycol. Hydroxycarboxylic acids may also be used in the production of polyesters provided that the acid and the conditions are selected so that the tendency for polycondensation is greater than the tendency for ring formation and provided that sufficient quantities of glycol are present to guarantee the presence of terminal hydroxyl groups. In addition, mixtures of various acids and glycols may be used, in which case mixed polyesters are obtained. Instead of the acids and glycols, other difunctional reactants may also be used in relatively small quantities. Examples of such difunctional reactants are compounds containing aromatic nuclei, such as phthalic acid or terephthalic acid, aromatic or aliphatic diamines, such as phenylenediamines, naphthylenediamines, piperazine, ethylenediamine, and aminoalcohols, such as aminopropanol or ethoxyl aniline. Polycondensation of the reactive components takes place by heating at about 100° to about 250° C. The OH value of the polyesters should be between about 20 and about 100 (preferably between 40 and 60), their molecular weight advantageously being in the range from about 500 to about 6,000. Before the reaction with the urea- or biuret-containing isocyanate takes place, any moisture present in the polyesters should preferably be removed, for example, by heating in vacuo to about 100°-150° C. or by passing inert gases through at that temperature. The preferred acid is adipic acid and the preferred glycols are ethylene glycol and 1,2-propylene glycol.

It is often advantageous to use polycaprolactones as starting material, including, for example, those described in U.S. Pat. Nos. 3,169,945, 2,914,556, 2,890,208, and 2,878,236 or in British Patent 859,645.

A preferred application is in the preparation of cast elastomers in which polyester polyols or polyesters terminated by aromatic amino groups are used as NCO-reactive components. The polyester polyamines are preferably obtained in accordance with European Patent Application EP 219,035 by hydrolysis of isocyanate-terminated compounds. In this process, polyesters containing in particular two or three hydroxyl groups are used to prepare NCO prepolymers and, in a second step, the isocyanate groups are converted by hydrolysis into amino groups. Elastomers having excellent heat stability and excellent mechanical properties are obtained.

Mixtures of the above-mentioned compounds containing at least two isocyanate-reactive hydrogen atoms, for example, mixtures of polyethers and polyesters, may of course be used.

Low molecular weight chain-extending agents or crosslinking agents may be used as optional component (B) of the isocyanate-reactive component. These chain-extending agents or crosslinking agents are preferably at least difunctional compounds containing hydroxyl groups attached to aliphatic and/or cycloaliphatic groups and having molecular weights in the range from about 60 to about 499. Low molecular weight diols containing hydroxyl groups attached to aliphatic or cycloaliphatic groups are particularly preferred. Examples of such compounds include ethylene glycol, diethylene glycol, triethylene glycol, 1,4-butanediol, 2,3-butanediol, 1,5-pentanediol, 1,6-hexanediol, neopentyl glycol, 1,4-bis( 1,4-dihydroxycyclohexane, terephthalic acid bis($\beta$-hydroxyethyl) ester, 1,4,3,6-dianhydrohexitols, 1,4-monoanhydrotetritols, propylene glycol, tetrapropylene glycol, bis-2(hydroxyethyl)hydroquinone, and bis(2-hydroxyethyl) resorcinol. Suitable polyfunctional compounds include trimethylol propane, trimethylol ethane, and 1,2,6-hexanetriol.

Diols containing additional groups may also be used, including, for example, adipic acid bis(2-hydroxyethyl) ester, terephthalic acid bis(2-hydroxyethyl) ester, diol urethanes, diol ureas, or polyols containing sulfonate and/or phosphonate groups, such as 1,6-hexamethylene-bis(2-hydroxyethyl urethane), 4,4'-diphenylmethane-bis(2-hydroxyethyl urea), or the adduct of sodium bisulfite with 1,4-butanediol or alkoxylation products thereof. Other low molecular weight compounds are described in detail in German Offenlegungsschrift 2,854,384.

Low molecular weight aromatic diamines may be used as chain-extending agents, particularly when the modified NDI containing urea and biuret groups according to the invention is present in the form of a finely divided solid diisocyanate and the surface of the NDI particles has been "retarded" against the attack of NCO-reactive groups by an anti-diffusion layer in accordance with European Patent Application EP 103,323.

Aromatic polyamines may also include amines in which the amino group is attached to aromatic heterocyclic groups. Suitable aromatic polyamines include p-phenylenediamine, 2,4and/or 2,6-tolylenediamines, diphenylmethane-4,4'- and/or -2,4,'- and/or -2,2'-diamines, 3,3'-dichloro-4,4'-diaminodiphenylmethane, 3-($C_1$–$C_8$ alkyl)-4,4'-diaminodiphenylmethanes, 3,3'-di($C_1$–$C_4$ alkyl)-4,4 '-diaminodiphenylmethane, 3,3',5,5'-tetra alkyl)-4,4'-diphenylmethanes, 4,4'-diaminodiphenyl sulfides, sulfoxides, or sulfones, diamines containing ether groups according to German Offenlegungsschriften 1,770,525 and 1,809,172 (U.S. Pat. Nos. 3,654,364 and 3,736,295), 2-halo-1,3-phenylenediamines optionally substituted in the 5-position (German Auslegeschriften 2,001,772, 2,025,896, and 2,065,869), bisanthranilic acid esters (German Offenlegungsschriften 2,040,644 and 2,160,590), 2,4-diaminobenzoic acid esters according to German Offenlegungsschriften 2,025,900, and tolylenediamines substituted by one or two $C_1$–$C_4$ alkyl groups. Particularly preferred aromatic polyamines are 3,5-diethyl-2,4-and/or -2,6-diaminotoluene (particularly in the form of their technical 80/20 or 65/35 isomer mixtures), asymmetrically tetraalkyl-substituted diaminodiphenylmethanes such as 3,5-diethyl-3',5'-diisopropyl-4,4'-diaminodiphenylmethane and isomer mixtures thereof according to German Offenlegungsschrift 2,902,090, 4,4'-diaminobenzanilide, 3,5-diaminobenzoic acid $C_1$–$C_4$ alkyl ester, 4,4'- and/or 2,4'-diaminodiphenylmethane, o and naphthylene-1,5-diamine. Low molecular weight aromatic diamines, however, are less preferred chain extending agents.

The rate at which the components react with one another can be accelerated by addition of organic bases, such as tertiary amines, or by metal salts of organic acids. Suitable organic bases include hexahydrodimethylaniline, methyl piperazine, dimethyl piperazine, tribenzylamine, tetramethyl diaminodipropyl ether. Similar effects are obtained when using polyesters containing chemically bound basic reactive groups. Suitable metal salts of organic acids include tin(II) ethylhexoate or dibutyltin dilaurate.

Plasticizers, dyes, and fillers may readily be added at any preparatory stage. Suitable plasticizers include phthalic acid esters and organic sulfonamides. Sulfur-containing plasticizers, such as methylene-bisthioglycolic acid butyl ester, are particularly preferred. As with natural rubber, part of the fillers produce an improvement in the mechanical properties of the new rubber-elastic products. This enhancement applies, for example, to titanium dioxide, silicon dioxide, bentonite, calcium silicate, and carbon black. Glass fibers are incorporated, for example, either in the polyesters or the polyethers or in the NCO preadduct containing urea or biuret groups. Their excellent mechanical properties and their high stability towards organic solvents and oils enable the described rubber-elastic plastics to be used for a wide variety of applications, including, for example, roller coverings, elastic components for machines, seals, buffers, bellows, and coverings for ball mills, shoes or parts of shoes, balls, and cylinders.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Comparison Example 1 (not according to the invention)

A mixture of 210 g (1.0 mole) of 1,5-naphthylene diisocyanate ("NDI") and 2]0 g of methyl ethyl ketone was heated with stirring to 90°-100° C., giving a clear homogeneous solution of NDI. Water (3.6 g, 0.2 mole) was then added dropwise to the solution. A crystalline deposit soon began to form and, after isolation by filtration, was found to be N,N'-bis(5-isocyanate-1-naphthyl)urea ("NDI urea diisocyanate") (NCO 20.7%; calculated 21.3%). This substance showed extremely poor solubility in organic solvents. Even in the above reaction mixture, no dissolution occurred even after prolonged heating at 90° to 100° C. Instead, only a suspension of NDI urea diisocyanate in the solution of NDI in methyl ethyl ketone was obtained. Further workup was difficult because the solvent needed to be distilled off using a continuously increasing temperature. A suspension of NDI urea diisocyanate in solvent-free NDI melt was finally obtained as an heterogeneous end product.

Comparison Example 2 (not according to the invention)

NDI (210 g, 1.0 mole) (m.p. 127° C.) was heated to a temperature of 130°-140° C. After approximately 1 hour, water (3.6 g, 0.2 mole) was added dropwise to the now molten polyisocyanate. A certain amount of the unreacted water, however, evaporated and condensed on the colder parts of the reaction vessel or escaped in gaseous form and condensed partly on the reflux condenser and partly on the glass wall. In addition, NDI sublimed to a considerable extent as the reaction temperature increased. An NDI sublimate was, therefore, also gradually deposited as a matted coating on the relatively cooler glass wall, where it reacted with the condensed water to form completely insoluble NDI polyurea that gradually detached from the glass wall and fell into the reaction mixture. Accordingly, this process is not useful. That is, this process takes place uncontrollably, with exact dosage of the water being impossible.

After the evolution of carbon dioxide stopped, an end product was obtained in which NDI polyurea was still present in significant amounts as a completely insoluble constituent.

Example 3

Preparation of a modified 1,5-naphthylene diisocyanate containing urea and biuret groups according to the invention NDI (2100 g, 10.0 mole) was heated to 130°-140° C. in a three-necked flask equipped with a stirrer, thermometer, and reflux condenser. After the isocyanate melted, a mixture of water (27 g, 1.5 mole) and dioxane (81 g) (water:dioxane ratio of 1:3) was added dropwise over a period of 1 to 2 hours. No visible precipitation of water on the colder glass walls of the reaction vessel was observed. The deposition of NDI associated with sublimation was prevented because the hot solvent dioxane, even when used in small quantities, prevented the precipitation of NDI on the glass walls. The reaction of water with NDI could be followed by monitoring the evolution of $CO_2$ gas. After about 4 hours, approximately 34.5 liters of $CO_2$ were evolved at 130° to 140° C. The dissolved $CO_2$ gas and the dioxane solvent were then removed under aspirator vacuum at constant temperature, and the liquid contents of the flask were poured onto a cold support. After the melt cooled, the modified NDI could readily be ground to a smaller size. The product had an NCO content of 31.8%.

The disadvantages described for Comparison Example 2 do not arise in this process.

A few additional modified isocyanates containing urea or biuret groups were prepared as described above using the quantities of NDI, water, and dioxane listed in the following Table I. (Product B is the product described immediately above.)

TABLE I

| | Modified NDI's According to Example 3 | | | |
|---|---|---|---|---|
| Product | NDI (moles) | $H_2O$ (mole/g) | Dioxane (g) | % NCO |
| A | 1.0 | 0.1/1.8 | 5.4 | 34.6 |
| B | 1.0 | 0.15/2.7 | 8.1 | 31.8 |
| C | 1.0 | 0.2/3.6 | 18.0 | 29.4 |
| D | 1.0 | 0.3/5.4 | 27.0 | 26.5 |
| E | 1.0 | 0.4/7.2 | 27.0 | 24.5 |

Example 4

An ethylene glycol/adipic acid polyester (200 g) o having an OH value of 56 (molecular weight 2,000) was dehydrated at 130° C. at 15 mm pressure. A 57.5 g portion of the modified isocyanate C (according to Example 3, NCO 29.4%) was then introduced with stirring. The reaction temperature initially fell to about 120° C. After 10 to ]5 minutes, when the temperature had risen again to around 128° C., the polyester (165 g) was added in molten form with stirring and the reaction mixture was poured into molds heated to 110° C. At a temperature of 120° C., the molding could be demolded after about 1 hour. The polyurethane elastomer was then conditioned for 5 to 8 hours at 110° to 120° C. The following mechanical values were measured after storage at room temperature for 1 week:

| | |
|---|---|
| Shore A hardness | 70 |
| Modulus | |
| at 100% (MPa) | 2.5 |
| at 300% (MPa) | 6.5 |
| Tensile strength (MPa) | 42.3 |
| Elongation at break (%) | 57.0 |
| Tear propagation resistance (KH/m) | 52.6 |
| Resilience (%) | 42 |

Example 5

An ethylene glycol/adipic acid polyester (200 g) having an OH value of 56 was dehydrated as in Example 4 and then homogeneously mixed at 60°-80° C. with a 27.7 g portion of the o modified isocyanate B (according to Example 3, NCO 31.8%). The modified NDI was milled to a particle size of 20 to 50 μm in a suitable mill (for example, a centrifugal ball mill). A suspension of the isocyanate in the polyester was obtained. This suspension remained stable for several hours at the above-mentioned temperature, so that no difficulties were encountered during subsequent processing. After brief degassing, the mixture was poured into a mold heated to 110° C. and then heated at 130°–150° C. After approximately 1 hour, the test specimen could be demolded and was conditioned for 3 to 4 hours at 120° C.

The following hydroxy compounds of relatively high molecular weight (that is, molecular weights 2,000; OH value 56) were processed by this method.

a. Polyester of adipic acid and ethylene glycol (see Examples 4 and 5)
b. Polyester of adipic acid and a mixture of ethylene glycol and 1,4-butanediol (molar ratio of 1:1)
c. Polyester of adipic acid and a mixture of ethylene glycol, 1,4-butanediol, and 1,6-hexanediol (molar ratio of 1:1:1)
d. Polyester of adipic acid and 1,6-hexanediol
e. Polyester of carbonic acid and 1,6-hexanediol (prepared by reaction of 1,6-hexanediol with diphenyl carbonate)
f. Polytetrahydrofuran The mechanical values shown in Table II were measured after the elastomers had been stored for about 1 week.

TABLE II

| Properties of Elastomers According to Example 5 | | | | | | |
|---|---|---|---|---|---|---|
| | Hydroxy compound | | | | | |
| | a | b | c | d | e | f |
| Shore A hardness | 70 | 75 | 78 | 72 | 73 | 75 |
| Modulus | | | | | | |
| at 100% (MPa) | 3.0 | 3.5 | 3.5 | 2.8 | 4.0 | 3.9 |
| at 300% (MPa) | 6.5 | 6.4 | 6.4 | 6.1 | 8.6 | 8.4 |
| Tensile strength (MPa) | 45.5 | 27.5 | 28.7 | 23.9 | 30.2 | 37.5 |
| Elongation at break (%) | 680 | 570 | 500 | 565 | 580 | 380 |
| Tear propagation resistance (KN/m) | 75.6 | 35.8 | 32.7 | 35.7 | 39.5 | 27.5 |
| Resilience (%) | 45 | 47 | 40 | 48 | 50 | 61 |

Example 6

A polyester of adipic acid and ethylene glycol (200 g) (according to Example 4) was homogeneously mixed at 60°–80° C. with the modified NDI's B, C, D, and E (according to Example 3) at an NCO:OH ratio of 1.05, again using a finely ground NDI product (particle size 20–50 μm). Before the powder was added, 0.7 g of the aliphatic diamine isophoronediamine (that is, 5-amino-3-(aminomethyl)-1,1,3-trimethylcyclohexane, or "IPDA") was added to the polyester melt. As a result of this measure, the polyisocyanate powder added was present in deactivated (retarded) form after the reaction with the aliphatic diamine IPDA (that is, anti-diffusion layer according to European Patent Application 103,323 and U.S. Pat. No. 4,483,974).

The polyester("PE")/polyisocyanate suspensions were stable in storage at room temperature or slightly elevated temperature. They could be further processed at any time by heat shock (130°–150° C.). Elastomers showing the mechanical values after storage for 1 week at room temperature (Table III) were obtained as described above.

TABLE III

| Deactivated Modified NDI's According to Example 6 | | | | |
|---|---|---|---|---|
| | Modified NDI | | | |
| | B | C | D | E |
| (Ratio of deactivated material to polyester) | (27.7 g/ 200 g PE) | (30.0 g/ 200 g PE) | (33.3 g/ 200 g PE) | (36.6 g/ 200 g PE) |
| Shore A hardness | 73 | 74 | 77 | 79 |
| Modulus at 100% (MPa) | 2.8 | 2.9 | 3.6 | 3.8 |
| Tensile strength (MPa) | 39.6 | 38.7 | 37.8 | 25.8 |
| Elongation at break (%) | 650 | 650 | 650 | 720 |
| Tear propagation resistance (KN/m) | 65.6 | 60.3 | 58.5 | 59.0 |
| Resilience (%) | 46 | 45 | 45 | 40 |

Example 7

Isophoronediamine (1.5 g) was added at 60°–80° C. to 200 g of a polyether (NH value 47) terminated by aromatic NH$_2$ groups. The amine-terminated polyether waS obtained by alkaline hydrolysis of an NCO prepolymer of a polypropylene glycol ether (OH value 56, molecular weight 2,000) and 2,4-diisocyanatotoluene. A 26.7 g portion of the product B (according to Example 3) was then added in ground form with stirring. The resultant suspension was easy to process because the anti-diffusion layer formed on the surface of the NDI particles considerably deactivated the NCO groups with respect to their reactivity with the aromatically bound NH2 groups. Even at 60°–80° C., no preliminary reaction leading to a pronounced increase in viscosity was observed. The reaction mixture thus stabilized could be degassed in an aspirator vacuum and processed to elastomers as described above.

The following mechanical values were obtained:

| | |
|---|---|
| Shore A hardness | 91 |
| Modulus at 100% (MPa) | 10.7 |
| Tensile strength (MPa) | 42.3 |
| Elongation at break (%) | 550 |
| Tear propagation resistance (KH/m) | 57.5 |
| Resilience (%) | 56 |

What is claimed is:

1. A process for the preparation of a modified 1,5-naphthylene diisocyanate containing urea and biuret groups comprising reacting
   (a) 1,5-naphthylene diisocyanate in molten form with
   (b) a mixture comprising 0.02 to 0.5 mole of water per mole of 1,5-naphthylene diisocyanate and 1 to 10 parts for each part of water of an organic solvent wherein the organic solvent has a boiling range of 80° to 140° C. or forms an azeotropic mixture with water having a boiling range of 80° to 140° c.

2. A process according to claim 1 wherein 0.1 to 0.25 mole of water per mole of 1,5-naphthylene diisocyanate is used.

3. A process according to claim 1 wherein 2 to 5 parts of an organic solvent for each part of water are used.

4. A process according to claim 1 wherein the reaction is carried out at a temperature in the range of 130° C. to 160° C.

5. A process according to claim 1 wherein the reaction is carried out at a temperature in the range of 130° C. to 140° C.

6. A process according to claim 1 wherein the organic solvent has a boiling range of 80° to 140° C.

7. A process according to claim 1 wherein the organic solvent has a boiling range of 100° to 120° C.

8. A process according to claim 1 wherein the organic solvent is water-miscible.

9. A process according to claim 1 wherein the organic solvent forms an azeotropic mixture with water having a boiling range of 80° to 140° C.

10. A process according to claim 1 wherein the organic solvent forms an azeotropic mixture with water having a boiling range of 100° to 120° C.

11. A process for the preparation of an elastomeric molding comprising reacting by the one-shot or prepolymer process at an isocyanate index of 70 to 130 a modified 1,5-naphthylene diisocyanate containing urea and biuret groups prepared according to the process of claim 1 with (A) a compound containing at least two isocyanate-reactive groups and having a molecular weight in the range from 500 to 10,000, and optionally, (B) an organic compound containing isocyanate-reactive groups and having a molecular weight in the range from 60 to 499, and (C) optional auxiliaries and additives.

12. A process according to claim 11 wherein the modified 1,5-naphthylene diisocyanate containing urea and biuret groups is used as a finely ground solid.

13. A process according to claim 12 wherein the modified 1,5-naphthylene diisocyanate in solid form is deactivated by addition of an aliphatic diamine before the reaction is carried out.

* * * * *